(12) United States Patent
Hamonic et al.

(10) Patent No.: US 7,698,953 B2
(45) Date of Patent: Apr. 20, 2010

(54) DEVICE FOR MEASURING THE MECHANICAL LOAD EXERTED BY A FLUID USING AN ELECTROMECHANICAL TRANSDUCER

(75) Inventors: Bernard Hamonic, Paris (FR); Max Mastail, Les Touches (FR); Yves Mevel, Guilers (FR); Roland Person, Brest (FR); Jean-Yves Ragon, Le Bignon (FR); Alain Loussert, Guilers (FR)

(73) Assignees: Institut Francais de Recherche pour l'Exploitation de la Mer, Issy lex Moulineaux (FR); Institut Superieur de l'Electronique et du Numerique, Lille (FR)

(*) Notice: Subject to any disclaimer, the term of this patent is extended or adjusted under 35 U.S.C. 154(b) by 201 days.

(21) Appl. No.: 11/793,586

(22) PCT Filed: Dec. 20, 2005

(86) PCT No.: PCT/FR2005/051113

§ 371 (c)(1),
(2), (4) Date: Mar. 28, 2008

(87) PCT Pub. No.: WO2006/067357

PCT Pub. Date: Jun. 29, 2006

(65) Prior Publication Data

US 2008/0190215 A1    Aug. 14, 2008

(30) Foreign Application Priority Data

Dec. 21, 2004  (FR)  .................... 04 13632

(51) Int. Cl.
G01F 1/86 (2006.01)
(52) U.S. Cl. .................................................. 73/861.02
(58) Field of Classification Search ................ 73/61.71, 73/204.13, 861.02
See application file for complete search history.

(56) References Cited

U.S. PATENT DOCUMENTS

| 4,065,969 A | 1/1978 | Dinwiddie |
| 4,257,260 A | 3/1981 | Beatson et al. |
| 6,122,956 A * | 9/2000 | Klausner et al. ........... 73/61.71 |
| 7,059,185 B2 * | 6/2006 | Gerhardt et al. .......... 73/204.13 |

FOREIGN PATENT DOCUMENTS

| DE | 102 32 233 C1 | 10/2003 |
| FR | 2 763 687 | 11/1998 |
| WO | WO 02/39143 A2 | 5/2002 |

* cited by examiner

*Primary Examiner*—Jewel Thompson
(74) *Attorney, Agent, or Firm*—Leffert Jay & Polglaze, P.A.

(57) ABSTRACT

A measuring device comprising: a sensor (1) with at least one electromechanical transducer (10); at least one electrical generator connected to said transducer; and means for measuring the electrical input impedance of the transducer. Said sensor (1) has an empty space (12) passing therethrough within which a substance (14) can flow, and said transducer (10) is situated at the periphery of said empty space (12) in such a manner as to be subjected to a mechanical load characteristic of the substance (14) flowing in said space (12), the measured electrical impedance being a function of said load. The device is suitable for use in a measuring apparatus seeking to determine the density of the substance (14) flowing inside said tubular space (12).

16 Claims, 7 Drawing Sheets

A: $\quad Ze = jC_0\omega + \dfrac{1}{r + j(l\omega - \dfrac{1}{c\omega})}$

B: $\quad Ze = jC_0\omega + \dfrac{1}{Z + r + j(l\omega - \dfrac{1}{c\omega})}$

DEVICE FOR MEASURING THE MECHANICAL LOAD EXERTED BY A FLUID USING AN ELECTROMECHANICAL TRANSDUCER

The invention relates to a measuring device of the type comprising: a sensor with at least one electromechanical transducer; at least one electrical generator connected to said transducer; and means for measuring the electrical input impedance of the transducer. The invention also relates to measuring apparatus fitted with such a device.

Such a measuring apparatus serves in particular to determine the density $\rho$ of a liquid or pasty substance flowing continuously inside a pipe, and it can find applications in the agri-food, cosmetic, or plastics fields, enabling the substance to be characterized better directly in a manufacturing line, and thus enabling better control to be obtained over the quality of the resulting substance.

French patent application FR 2 763 687 describes an appliance of that type that enables the density $\rho$ of a fish paste to be determined, the paste being constituted essentially by a mixture of water, air, salt, and fish fibers, with the determination being done at the outlet from an extruder. The apparatus is used in a pipe situated downstream from the extruder and having the fish paste flowing inside it. The apparatus comprises a piezoelectric pellet acting as an electromechanical transducer placed inside the pipe, in a plane containing the axis thereof.

In practice, using the apparatus of FR 2 763 687 raises the following problems: it is found that the piezoelectric pellet (and its connections) disturb the flow of fish paste since the pellet obstructs the pipe and separates the stream of paste into two portions. In addition, the pellet becomes clogged up very quickly, leading firstly to errors in estimating the density $\rho$ of the paste, and secondly to problems of bacterial contamination.

The invention seeks to remedy those problems, or at least to attenuate them.

To achieve this object, the invention provides a measuring device of the above-specified type, wherein said sensor has an empty space passing therethrough within which a substance can flow, and wherein said transducer is situated at the periphery of said empty space in such a manner as to be subjected to a mechanical load characteristic of the substance flowing in said space, the measured electrical impedance being a function of said load.

By means of the invention, said transducer (and thus its connections) lie at the periphery of the empty space in which the substance flows. The flow of substance is thus less disturbed than it is by the piezoelectric pellet of FR 2 763 687, and the transducer is less subjected to clogging.

In order to disturb the flow of substance as little as possible, the transducer projects little or not at all into the inside of the empty space, and it may even be set back a little from said space.

Only one of the faces of the transducer is exposed to the substance and is subjected directly to said mechanical load. In the present application, this exposed face is referred to as the "first" face of the transducer. Advantageously, the connections of the transducer are preferably provided mainly on a non-exposed face, referred to as the "second" face.

It should be observed that the transducer(s) need not necessarily be placed all around the empty space: it/they could be located solely on one side of the face. When the transducers are distributed all around the empty space, they may be distributed in regular or other manner.

Advantageously, said empty space is generally tubular in shape (i.e. it is not bent) in order to disturb the flow of substance passing therethrough as little as possible.

It should be observed that a tubular empty space is not necessarily circular in section. The empty space may have a section that is rectangular, square, polygonal, elliptical, . . . . Similarly, the axial length of the tubular space is not necessarily greater than the longest dimension of its section. Advantageously, the empty space is of section substantially identical to that of the pipe in which the device is connected so as to disturb the flow as little as possible.

The general operating principle of such a measurement device is the following: the mechanical load exerted on the transducer by the substance flowing inside the tube prevents the transducer from vibrating freely and thus modifies its electrical behavior. This causes the value of the electrical input impedance of said transducer to vary, which value is measured. Thereafter, the value of this electrical impedance makes it possible by calculation to determine the density of the substance in question, providing the propagation speed of a wave train passing through the substance is also known.

Advantageously, the sensor comprises a plurality of transducers distributed around the tubular space.

The transducers may be connected in series or in parallel. Either way, they are electrically dependent and equivalent to a single transducer measuring a mean mechanical load.

Alternatively, the transducers may be electrically independent, i.e. each may be connected to its own generator, or they may be connected to a common generator via a multiplexer or via any other system enabling each transducer to be powered in succession. Under such circumstances, said impedance measurement means measure impedance for each circuit independently.

Electrically independent transducers serve to multiply the number of measurement points and thus to characterize the substance flowing along the pipe in a plurality of radial directions. The term "radial direction" is used in the present specification to designate a direction perpendicular to the main axis of the tubular space. Thus, when the pipe is placed horizontally, it becomes possible to characterize separately the portion of the substance flowing in the top of the pipe and the portion flowing in the bottom of the pipe. It is also advantageous for the electromechanical transducers to be distributed regularly in different radial directions at the periphery of the tubular space.

Also advantageously, the or each transducer comprises a sensitive element made of piezoelectric material, referred to below as a piezoelectric element, thus making it possible to obtain sensors that are simple and compact in structure. In the description below, details are given solely of transducers of this type. Nevertheless, other types of electromechanical transducer could be used, i.e. transducers capable of receiving energy from an electrical system and delivering energy to a mechanical system, or vice versa.

In an embodiment of the invention, the first face of the or each transducer defines the tubular space: it constitutes a wall of said space. Thus, the first face is substantially neither set back from nor projecting into said space, so the risks of clogging are diminished. To further diminish the risks of clogging and to make the first face easier to clean, it may be covered by an anti-adhesive coating such as polytetrafluoroethylene (PTFE) (better known under the trademark "Teflon"), or some analogous material. PTFE also presents the advantage of being compatible with agri-food standards.

In another embodiment, the first face of the transducer is covered by a membrane. It is then the membrane that defines the tubular space. The membrane must be sufficiently flexible to enable the transducer to detect the mechanical load exerted by the substance flowing in said space. Furthermore, the membrane must not prevent the transducer from vibrating.

The invention also provides a measuring apparatus comprising: a measuring device as defined above; means for measuring the propagation speed of a wave train passing through the substance flowing in said empty space or in a pipe portion situated upstream or downstream from said space; and a calculation unit for determining the density of said substance from the measured propagation speed and impedance.

The measuring apparatus is for installing in an existing pipe, the empty space of said sensor being placed between two portions of said pipe and interconnecting these two pipe portions, an upstream portion and a downstream portion, via said tubular space. Alternatively, the measuring apparatus may have one or two pipe portions on either side of said sensor and the assembly constituted by the sensor and the pipe portions is installed to take the place of a segment of the existing pipe.

The invention and its advantages can be better understood on reading the following detailed description of examples of the invention, given in non-limiting manner. The description refers to the accompanying sheets of figures, in which.

Figure 1:
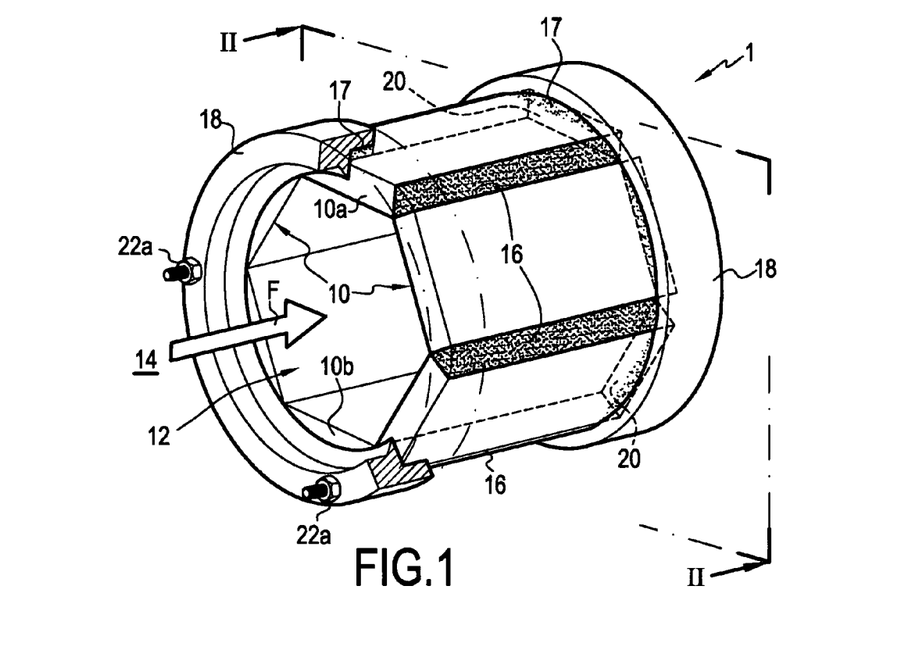
FIG. 1 is a perspective view of a first example of a sensor that can be fitted to a measurement device of the invention.
Figure 2:
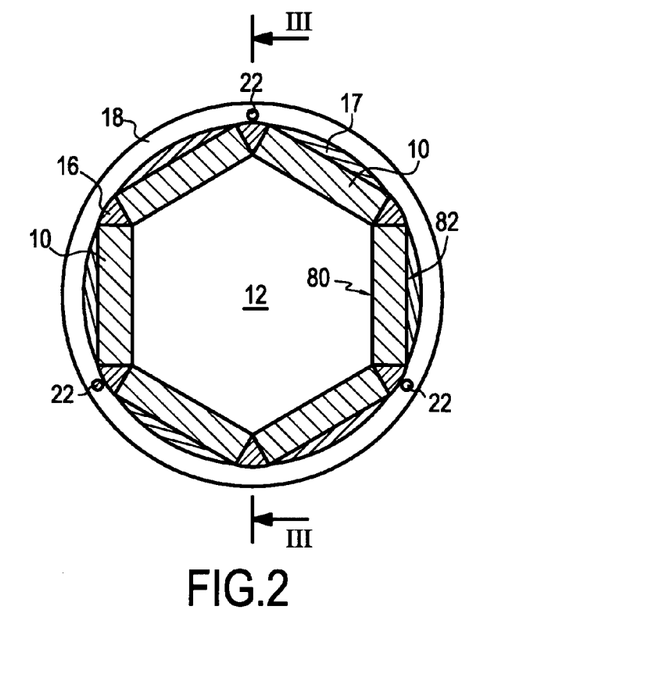
FIG. 2 is a section on plane II-II showing the FIG. 1 sensor.
Figure 3:
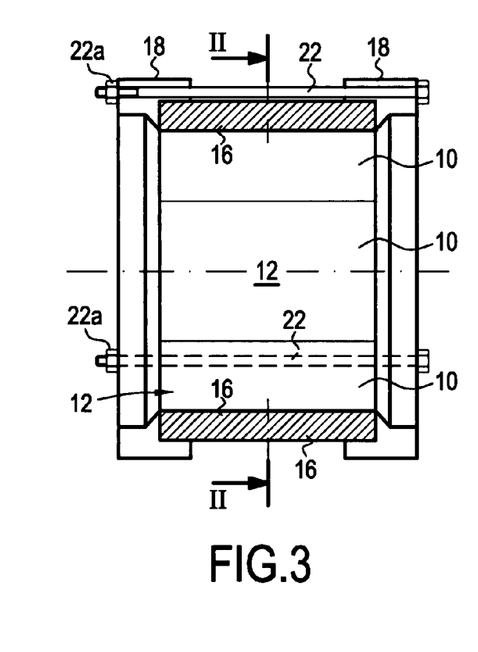
FIG. 3 is a section on plane III-III showing the FIG. 1 sensor.

FIGS. 1, 2, and 3 show a first example of a sensor 1 comprising a plurality of transducers constituted by piezoelectric elements 10 in the form of plates, such as ceramic plates. Such transducers also include connections (not shown) associated with the elements 10.

The type of ceramic used for the piezoelectric elements 10 is selected as a function of the mechanical loading these elements are to withstand from the substance (where the loading depends on the density $\rho$ of the substance). When the substance is an agri-food substance such as a fish paste, it is possible for example to use a ceramic of the PZ35 type, sold by the supplier Ferroperm.

The elements 10, of which there are six in the example shown, are joined together edge to edge to define between them a tubular empty space 12 of hexagonal section through which a liquid or pasty substance 14 is to pass, traveling in the direction of arrow F. In order to guarantee that the space 12 is leaktight, sealing gaskets 16 are disposed between pairs of adjacent elements 10. The elements 10 are held in place by two sleeves 18 that surround the ends of the sensor 1. Recesses 20 may be formed in the sleeve 18 to facilitate positioning the elements 10. The elements 10 must in any event remain free to vibrate. The sleeves are thus preferably made of elastomer.

As shown in FIG. 2, a gasket 17, e.g. a silicone gasket, may be placed around the elements 10, between them and the sleeves 18.

Usually, in order to ensure good operating conditions, it is preferable to prestress the elements 10 a little. Thus, rods 22 are used interconnecting the sleeves 18. These rods are threaded over respective end portions to enable respective nuts 22a to be tightened or loosened so as to move the sleeves 18 towards or away from each other, thereby clamping the elements 10 to a greater or lesser extent along the main axis of the tubular space. It should be observed that it is desired mainly to prestress the elements 10 radially (i.e. in the thickness direction thereof). This small radial prestress is obtained by the above-mentioned clamping, which leads to a very small amount of radial deformation of the elements. The rods 22 also serve to hold the sleeves around the elements 10.

Advantageously, the sleeves 18 are made of an insulating elastomer material and said material is selected so as to be capable of withstanding the temperatures of the substances that are to flow through the space 12. For example, it is possible to use an acetyl resin such as "Delrin" (registered trademark) that can withstand temperatures up to 200° C.

The first faces 80 of the elements 10 face towards the inside of the space 12. These faces are subjected to the mechanical load exerted by the substance 14. The outside or second faces 82, opposite from the first faces 80, are free mechanically. A conductor wire (not shown) is connected to each face 80, 82. Connecting these wires does not present any particular problem given the nature of the ceramic material used for the elements 10. When the elements 10 are electrically independent, the conductor wires from each element are connected to a generator specific to that element or to a common generator via a multiplexer or a system of switches that are actuated in succession. When the elements are electrically dependent, then the first faces 80 and similarly the second faces 82 are electrically interconnected and connected to the generator.

Figure 4:
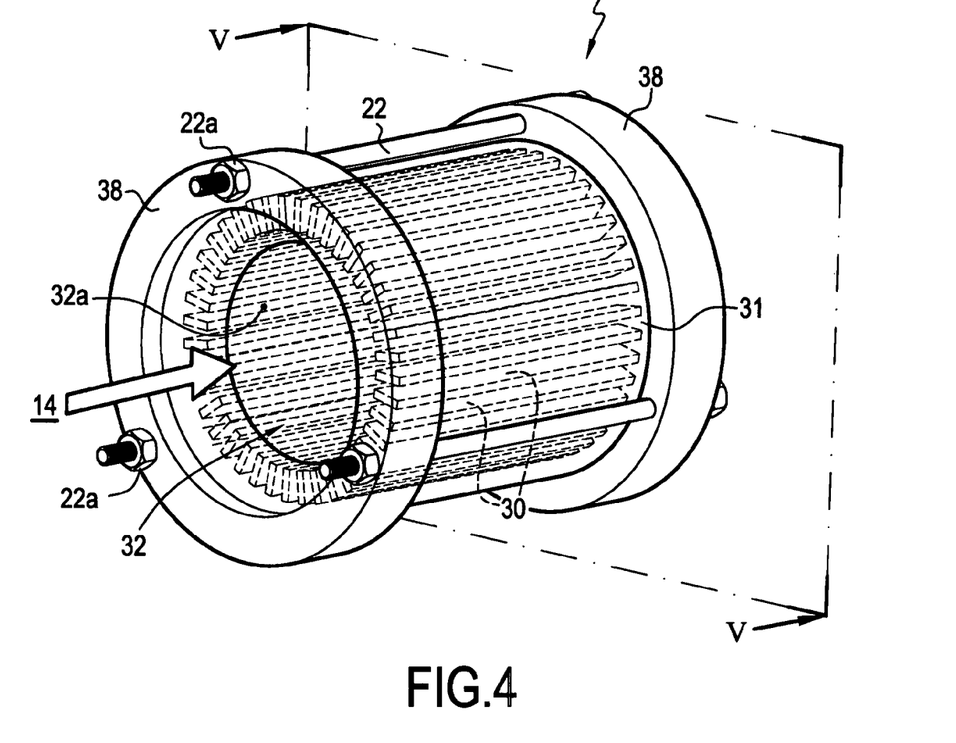
FIG. 4 is a perspective view of a second example of a sensor suitable for fitting to a measurement device of the invention.
Figure 5:
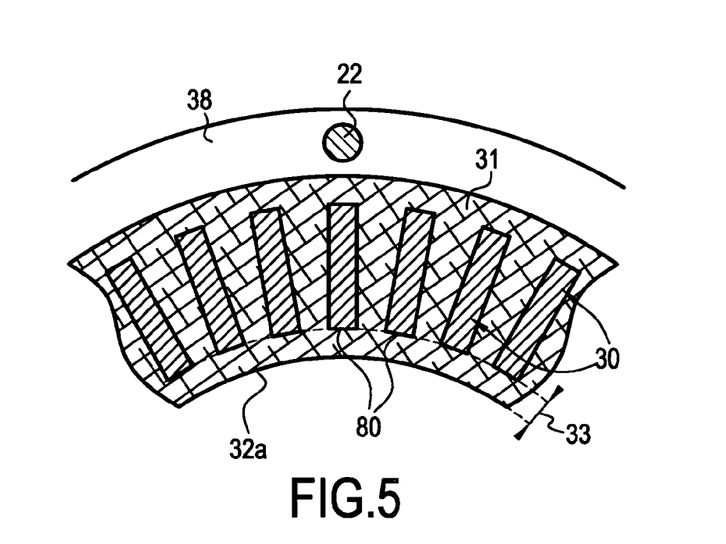
FIG. 5 is a section on plane V-V showing a portion of the FIG. 4 sensor.

FIGS. 4 and 5 show a second example of a sensor 3 that comprises a plurality of piezoelectric elements 30 in the form of sticks embedded in a matrix 31. The matrix 31 may be made of epoxy resin and molded around said elements 30. The elements 30 may be completely embedded in the matrix 31, as shown in FIG. 5, or they may be embedded in part only. The material of the matrix 31 is selected to be sufficiently flexible to allow the elements 30 to vibrate and be sensitive to the mechanical load exerted by the substance 14. A tubular space 32 passes through the sensor 3. The walls 32a of this space are formed by the matrix 31.

The elements 30 are regularly distributed around the periphery of said space and they may be electrically independent or dependent, as explained above. The first faces 80 are separated from the walls 32a by a portion of the matrix 31 that can be thought of as a membrane 33 covering the faces 30.

The composite structure (matrix 31/elements 30) of this second example of a sensor makes it easy to fabricate transducers in a variety of shapes.

The sensor 3 may present sleeves 38 at its ends, which sleeves are used for connecting the sensor 3 to a pipe. The sleeves 38 may be molded with the composite body of the sensor, or they may be parts fitted to said body, as shown in the figure. There can be seen rods 22 analogous to those described above.

Figure 6:
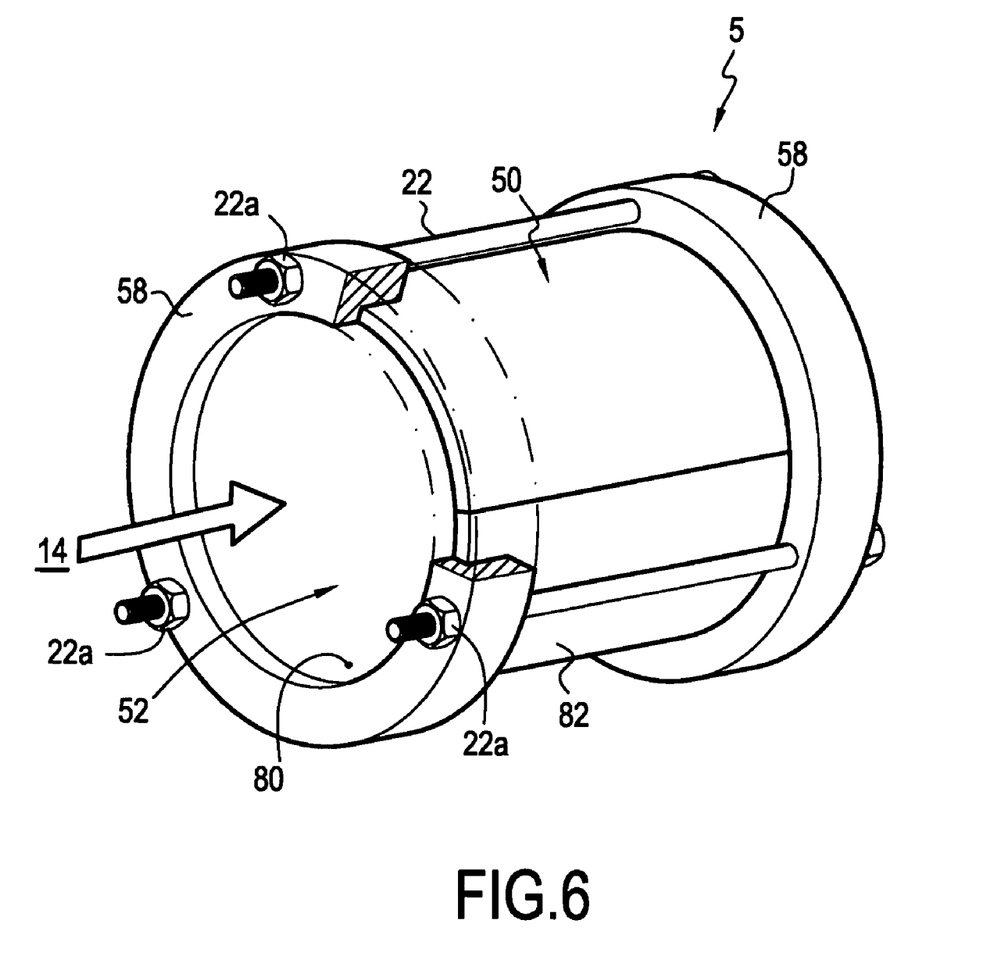
FIG. 6 is a perspective view of a third example of a sensor suitable for fitting to a measurement device of the invention.

FIG. 6 shows a third example of a sensor comprising a single piezoelectric element 50 that is rolled up so as to define a tubular space 52. By way of example, the piezoelectric element 50 is made of polyvinylidene fluoride (PVDF). It can be made in the form of a plate and then deformed (curved), the edges of the plate being united so as to form a cylindrical tube as in the example shown (a sealing gasket can be placed between said edges). It is also possible to make a PVDF sensor directly in the desired shape. Either way, sleeves 58 can be placed at the ends of the sensor, either to hold the element 50 in its deformed position, or to make it easier to connect the sensor between two pipes. It should be observed that a single central sleeve surrounding the element 50 could be used instead of two end sleeves 58.

Two conductor wires (not shown) are connected respectively to the first face 80 (i.e. the inside face) of the element 50 that defines the space 52 (the face 80 is a wall of the space 52), and to the second face 82 (i.e. the outside face) of the sensor 5. These conductor wires are connected to a generator, and to means for measuring the output impedance from the generator.

The second and third sensor examples 3 and 5 have the advantage of being completely circularly cylindrical, thus making it possible to avoid retaining any substance.

Figure 7:
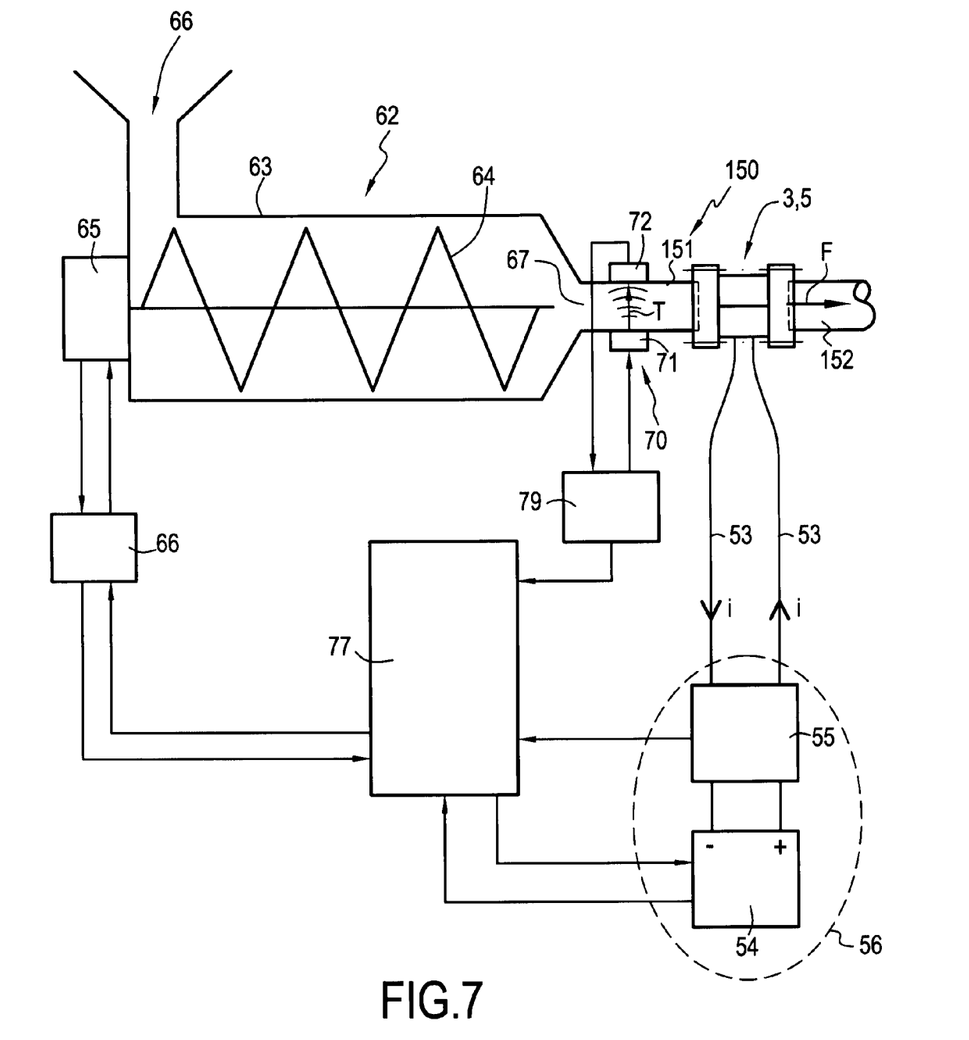
FIG. 7 is a diagram showing an example of measuring apparatus of the invention.

FIG. 7 is a diagram of an example of measuring apparatus 150 of the invention, mounted at the outlet from an extruder 62.

The extruder 62 comprises a cylindrical body 63 within which an extrusion screw 64 turns under drive from a motor 65. The raw materials penetrate into the body 63 via a feed hopper 66 and leave it in the form of a shaped substance 14 via the outlet 67. The substance 14 may be a fish paste product, or any other liquid or pasty mixture, in the agri-food business, or otherwise.

The measuring apparatus 150 comprises a measurement device of the invention fitted with a sensor 1, 3, or 5 of the type described above, an electrical generator 54 connected to the transducer(s) of the sensor 1, 3, 5 via two conductor wires 53, and means 55 for determining the electrical impedance Ze at the outlet from the generator, such an impedance bridge or any other impedance-measuring system. For simplification purposes, mention is made below of an impedance meter 55.

Relative to the flow direction of the stream F of substance, the sensor is connected to upstream and downstream pipe portions 151 and 152.

It should be observed that the generator 54 is directly connected to the transducer(s) of the sensor 1, 3, 5 by the conductor wires 53. In FIG. 7, the flow direction of the electrical current i is represented during a positive half-cycle of the sinusoidal signal delivered by the generator 54, corresponding to the + and − signs marked thereon. The impedance meter 55 measures the impedance at the input(s) of the transducer(s), corresponding to the impedance at the output from the generator. In general, it should be observed that regardless of the components placed between the output of the generator and the input(s) of the transducer(s), these impedances are related, and measuring one of them enables the other to be determined by calculation. In addition, in a particular embodiment, a single system 56 includes both a generator 54 and the impedance meter 55, and thus serves simultaneously to deliver electrical current and to measure impedance.

The upstream portion 151 is connected to the outlet 67 of the extruder 62 and the two pipe portions 151 and 152, preferably of the same size, are connected to each other by said sensor 1, 3, or 5 via the tubular space 12, 32, or 52 passing therethrough.

The sleeves 18, 38, or 58 disposed at each end of the sensor 1, 3, or 5 facilitate making connections to the pipe portions 151 and 152, and advantageously the section of the tubular space 12, 32, or 52 is substantially identical to that of the pipes 151 and 152. Selecting a section that is substantially identical serves to avoid forming a bottleneck that would disturb the flow of substance 14 or an enlargement within which the substance could accumulate and stagnate. This does not exclude the possibility of selecting a tubular space having a section that is slightly greater than or slightly smaller than that of the pipes 151 and 152. Such a situation would occur more particularly when the section of the tubular space is polygonal while the section of the pipe is circular, as applies to FIGS. 1 to 3.

As explained above, no portion of the sensor 1, 3, or 5 is located within the stream F of substance 14 traveling along the pipe portions 151 and 152.

Advantageously, the sensor 1, 3, or 5 can be separated from the pipe portions 151 and 152 so as to be cleaned more easily. For example, the pipes 151 and 152 can be merely received in recesses in the sleeves 18, 38, or 58.

The measuring apparatus 50 also includes means 70 for measuring the propagation speed CL of a wave train passing through the substance 14 traveling along the empty space 12, 32, or 52 in the sensor 1, 3, 5 or in one of the pipe portions 151, 152, the wave train passing through the substance 14 in a transverse direction T that is perpendicular to the main axis of the portions 151 or 152 or of said empty space.

In an embodiment, these means 70 comprise an ultrasound emitter 71 and an ultrasound receiver disposed facing each other at the periphery of the empty space or of a pipe portion 151, 152 situated upstream or downstream from said space. In the figure, the emitter 71 and the receiver 72 are disposed on the upstream portion 151. The means 70 also include a calculation unit 77 connected to the receiver 72 and to the emitter 71 via a member 79 for emitting and receiving the signal. The member 79 issues soundwave emission orders to the emitter 71 and calculates the time delay between emission and reception of the soundwave. Given the distance between the emitter 71 and the receiver 72, the member 79 can determine the propagation speed CL of the soundwave passing through the substance 14 in the direction T. This speed CL is communicated to the calculation unit 77.

In another embodiment that makes use of the above-described first example sensor 1, the means 70 for determining the propagation speed CL comprise two of the piezoelectric elements 10 of the sensor 1 that are situated facing each other. With reference to FIG. 1, they could be the elements 10a and 10b. One of the elements 10a is dedicated to emission and is subjected to a varying voltage at high frequency so as to emit an ultrasound wave, while the element 10b is dedicated to receiving said wave. The elements 10a and 10b performing functions analogous to those of the emitter 71 and the receiver 72 are connected to a calculation unit and to a signal emitter receiver member performing functions analogous to those of the members 77 and 79 as described above.

Figure 8A:
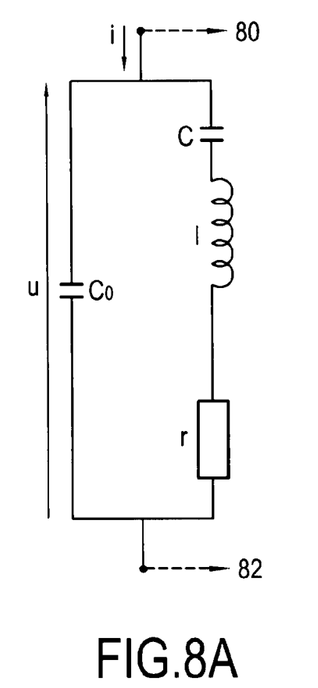
FIGS. 8A to 8C are equivalent electrical circuit diagrams for a transducer of the invention when empty and when loaded, and also showing formulae for calculating the input impedance of the transducer.
Figure 8B:
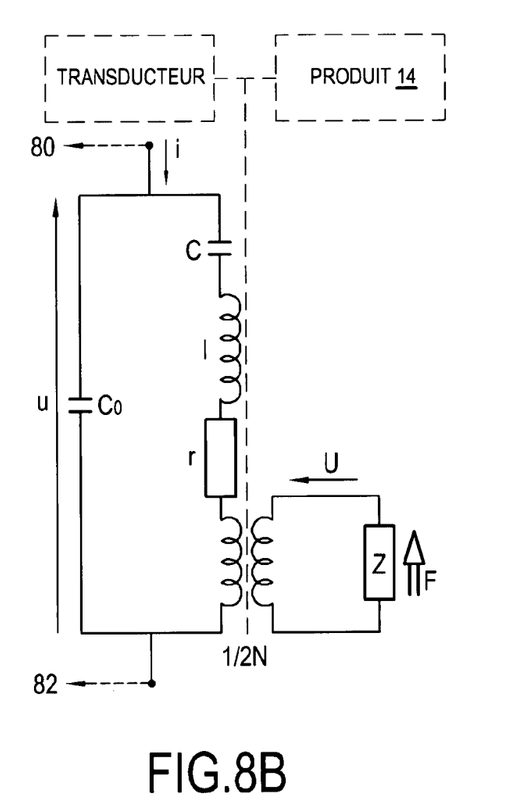
Figure 8C:
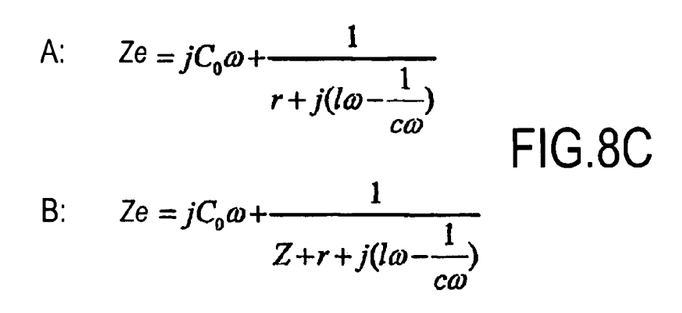

As explained in the French patent application published under the No. FR 2 763 687, on line 10, page 5 to line 15, page 6, and also in the scientific publication by Y. Mevel, M. Mastail, R. Baron, "Measurement of acoustic impedance to estimate the fish sol density", SENSORAL 98, Montpellier Narbonne, Feb. 23-27, 1998, when the transducer(s) of the device of the invention is empty (i.e. when it is not subjected to the mechanical load characteristic of the substance 14), it is considered as being electrically equivalent to a series RLC circuit connected in parallel with a capacitor $C_0$, as shown in FIG. 8A. The electrical impedance Ze of the transducer is then given by formula A in FIG. 8C. Once loaded (i.e. when subjected to the mechanical load characteristic of the substance 14), the transducer is considered as being equivalent to the circuit shown in FIG. 8B and the electrical impedance Ze of the transducer is as given in formula B of FIG. 8C. This impedance depends on Z which characterizes the substance 14. By measuring the electrical impedance Ze, it is possible to calculate the acoustic impedance Za of the substance 14 covering the transducer. It happens that the impedance Za of the substance is given by the formula:

$$Za = \rho \times CL \times S$$

where S is the surface area of the first face 80 of the transducer (i.e. the exposed area of the piezoelectric element). Given Za, CL, and S, it is possible to determine the density $\rho$ of the substance 14.

When the measuring apparatus 150 is mounted downstream from an extruder 62, it is possible during manufacture of the mixture to respond to the measured value for density $\rho$ by acting immediately on the speed of rotation of the screw 64 so as to maintain the density $\rho$ of the mixture leaving the extruder 62 constant. To do this, the calculation unit 77 is connected to a control device 66 serving to adjust the speed of the motor 65 driving the screw 64.

Figure 9:
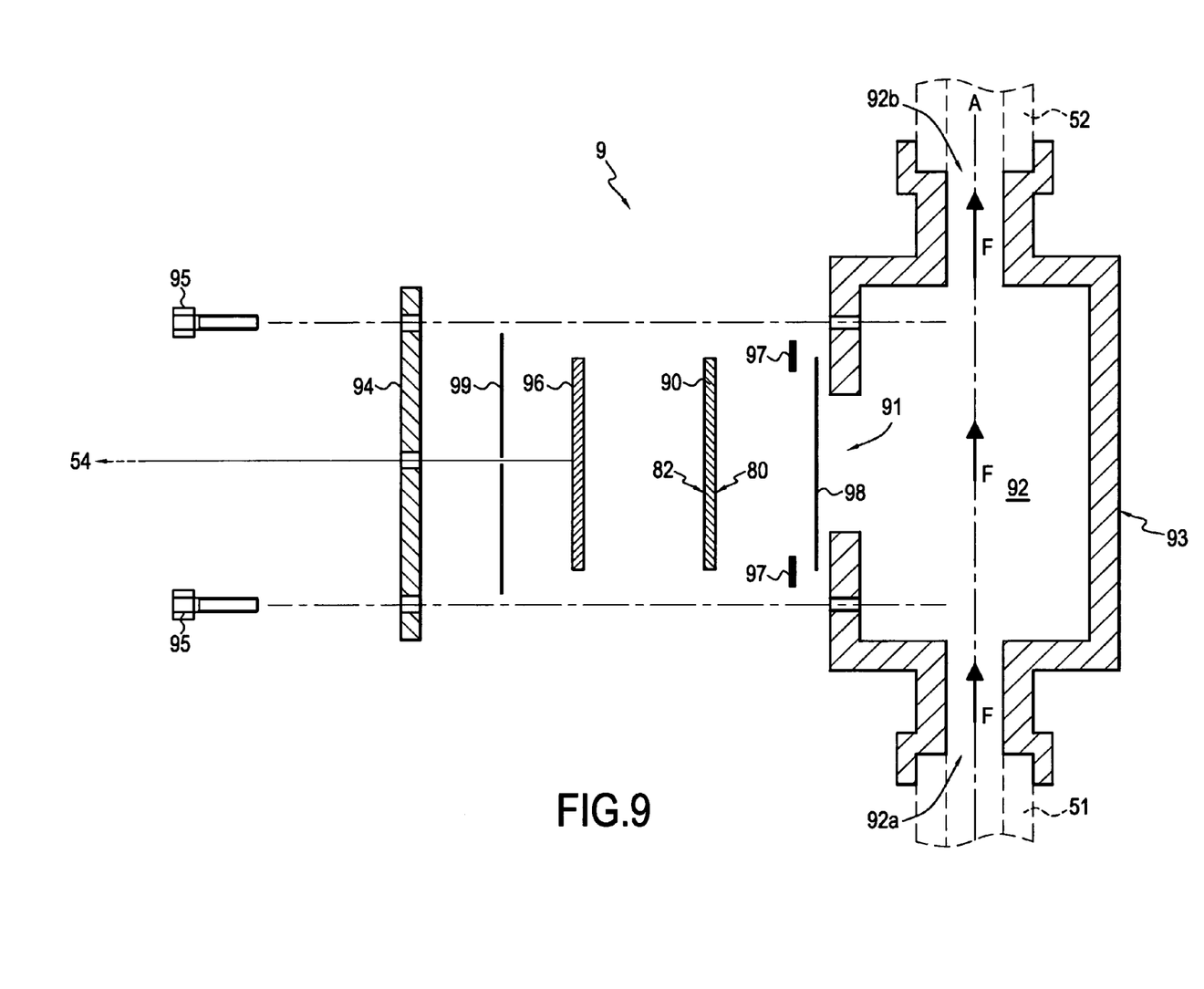
FIG. 9 is a diagram of a fourth example of a sensor of the invention.

FIG. 9 shows another example of a sensor 9 of the invention of the type comprising a hollow body 93 defining said empty space 92 in its inside and having at least one side opening 91 formed therein, which opening is covered by a sensitive plate 90 of piezoelectric material.

More particularly, the sensor 9 comprises a body 93 defining internally an empty space 92 through which the substance 14 for characterizing can flow. In FIG. 9, arrows F represent the stream of said substance 14.

A side opening 91 is formed in the body 93. In the present application, the term "side opening" is used to designate an opening other than via the inlet and outlet openings 92a and 92b of the empty space 92. In the example shown, the empty space 92 is tubular about an axis A. The inlet and outlet openings 92a, 92b are in alignment on the axis A and they extend perpendicularly thereto. The side opening 91 is parallel to the axis A.

The side opening 91 is covered by a stack structure comprising: a sensitive plate 90 of piezoelectric material having a first face 80 facing towards said empty space 92, and a second face 82 opposite thereto; a support plate 94 situated beside the second face 82; and fastener means 95 for fastening the support plate relative to the body 93.

When the stack structure is assembled, the sensitive plate 90 extends between the edges of the side openings 91 and the support plate 94. The fastener means 95 enable the assembled structure to be held together and fastened to the body 93. These fastener means 95 must also allow the sensitive plate 90 to vibrate. In the example, these fastener means are clamping screws 95 disposed at the periphery of the support plate 94 and co-operating with threaded housings formed in the body 93 around the side opening 91. These clamping screws 95 must be sufficiently loose to allow the plate 90 to vibrate. Advantageously, these screws 95 also enable the sensitive plate 90 to be prestressed a little, said prestress being radial, i.e. extending in the thickness direction of the plate 90. To control the magnitude of this prestress, which must remain small, the clamping screws 95 are tightened to a greater or lesser extent, while monitoring tightening, e.g. by means of a torque wrench.

Advantageously, the sensitive plate 90 is made of a piezoelectric polymer, in particular polyvinylidene fluoride (written PVDF or PVF$_2$) or else a copolymer of polyvinylidene fluoride and of trifluoroethylene, written P(VF$_2$-VF$_3$) or P(VDF-TrFE). The plate 90 of piezoelectric polymer forms an electromechanical transducer suitable for generating a potential difference as a result of deformation in its thickness direction. Piezoelectric polymer materials such as PVDF and copolymers thereof have piezoelectric properties that are not as great as those of ceramics, but they present several advantages: they can easily be made in the form of a film of large area and/or small thickness; they present a certain amount of flexibility in shaping; and they can be molded or thermoformed. In addition, since such polymers are more robust than ceramics, it is possible to use them without worry at higher tensions and thus obtain not only properties representative of the layer of substance 14 close to the sensor 9, but also an image of properties at greater depth in the stream of substance.

In order to polarize the sensitive plate 90, its first and second faces 80 and 82 are covered in a conductive surface coating. For example, they are metal-plated with a metal such as copper, nickel, silver, gold, or nickel-aluminum alloy. By way of example, such a coating can be obtained by vacuum metallization. Depending on the quality of the metallization, polarization is obtained that is of better or lesser quality. In general, a coating of silver makes it possible to obtain good polarization.

The stack structure also comprises first and second electrical connection means for connecting (directly or indirectly) said first and second faces 80 and 82 of the sensitive plate 90 to the electrical generator 54. Advantageously, the first connection means comprise a conductive plate 96 covering the second face 82 of the plate 90. By way of example, this plate 96 can be made of copper and, advantageously it can cover the second face 82 completely. The conductive plate 96 encourages uniformity and improves the quality of the impedance measurements performed by being insensitive to local variations in resistance over the second face 82. The plate 96 is electrically connected to one terminal of the generator 54. The first face 80 is put electrically into contact with the body 93 via conductive strips 97, e.g. made of copper, that are placed between the body 93 and the plate 90 at the edges of the opening 91. The body 93, the plate 90, and the support plate 94 and the clamping screws 95 are electrically in contact and they are connected to the other terminal of the generator 54.

Also advantageously, said stack structure includes at least one PTFE plate 98 covering the first face 80 of the sensitive plate 90 and acting as an anti-adhesive covering, in order to limit the extent to which said face 80 becomes clogged.

An insulating plate 99 is placed between the support plate and the conductive plate 96 so as to insulate the support plate 94 from the conductive plate 96. By way of example, this insulating plate 99 can be made of PTFE. Overall, the structure of the sensor of FIG. 9 is very simple and can be used for making reliable measurements.

In practice, the body 93 is installed between two pipe portions, an upstream portion 151 and a downstream portion 152, with the substance that is to be characterized flowing inside the empty space 92 defined by the inside of the body.

Figures 10, 11, 12:
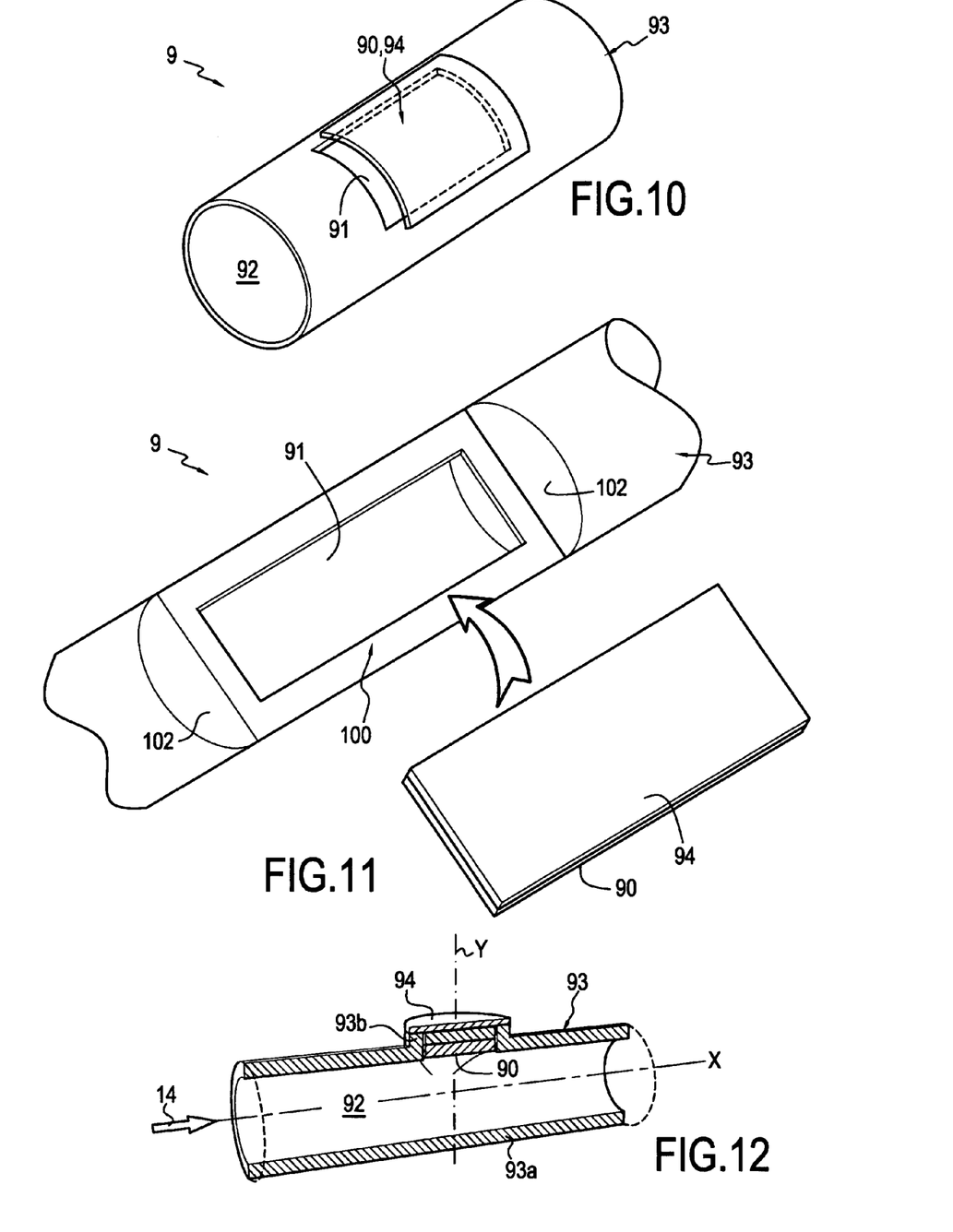
FIGS. 10 to 12 are diagrams showing a plurality of devices including a sensor of the type shown in FIG. 9.

Naturally, it is preferable to interfere with the flow of substance 14 as little as possible and to avoid creating spaces in which it can collect, in particular for reasons of hygiene. FIGS. 10 to 12 show various examples of devices that take these considerations into account.

The example of FIG. 10 comprises a body 93 that is generally in the form of a hollow cylinder of circular section. The various plates 90, 94 of the sensor 9 are curved so as to match the outside curvature of the body 93 when covering the side opening 91 formed therein. It should be observed that it is easy to give a curved shape to the sensitive plate 90 of the sensor when it is made of polymer material.

In the example of FIG. 11, a generally plane shape has been retained for the various plates 90, 94 of the sensor. The body 93 is generally in the form of a cylinder of circular section, and it presents a flat 100 in its wall. The junctions between the upstream and downstream edges of the flat and the wall of the body 93 are provided via chamfers 102. The side opening 91 in the body 93 is made in the flat 100, and the plates 90, 94 of the sensor are stacked on the flat 100.

Finally, in the example of FIG. 12, the body 93 is formed by uniting two hollow cylinders 93a and 93b of circular section, the first cylinder 93a having the substance 14 traveling therealong on its axis X, and the second cylinder 93b intersecting the first cylinder 93a, the axis Y of the second cylinder 106 being perpendicular to the axis X of the first. Some of the plates of the sensor, including the sensitive plate 90, are received inside the second cylinder 93b. The support plate 94 can be housed in the cylinder 93b or can cover the outside opening thereof, as shown.

It should be observed that in all of the example devices of FIGS. 10 to 12, the transducer of the sensor 9 (i.e. the sensitive plate 90) is situated at the periphery of the empty space 92 going through the sensor 9, in accordance with the invention.

The invention claimed is:

1. A measuring device comprising: a sensor with at least one electromechanical transducer; at least one electrical generator connected to said transducer; and means for measuring the electrical input impedance of the transducer, wherein said sensor has an empty space passing therethrough within which a substance can flow, and wherein said transducer is situated at the periphery of said empty space in such a manner as to be subjected to a mechanical load characteristic of the substance flowing in said space, the measured electrical impedance being a function of said load.

2. A measuring device according to claim 1, wherein said empty space is generally tubular in shape.

3. A measuring device according to claim 1, wherein said at least one transducer comprises a sensitive element made of piezoelectric material.

4. A measuring device according to claim 1, wherein said sensor comprises a plurality of transducers distributed around said empty space.

5. A measuring device according to claim 4, wherein said sensor comprises a plurality of transducers united edge to edge, defining between them said tubular space, a sealing gasket advantageously being disposed between each pair of adjacent transducers.

6. A measuring device according to claim 4, wherein said transducers are held in position by at least one sleeve.

7. A measuring device according to claim 1, wherein said sensor comprises a single transducer that is rolled up so as to define said empty space.

8. A measuring device according to claim 1, wherein said sensor comprises a plurality of transducers embedded in a matrix molded about them, said matrix defining said empty space.

9. A measuring device according to claim 1, wherein said sensor comprises: a body defining said empty space internally and having at least one side opening formed therein;
and a sensitive plate of piezoelectric material covering said side opening.

10. A measuring device according to claim 9, wherein said side opening is covered by a stack structure comprising: said sensitive plate of piezoelectric material having a first face facing towards said empty face and a second face opposite from the first face; a support plate situated beside said second face; and means for fastening the support plate relative to the body.

11. A measuring device according to claim 9, wherein said sensitive plate has a first face facing towards said empty space, and a second face opposite from the first face, and in that said sensitive plate is made of PVDF or of P(VDF-TrFE) copolymer, and in that its first and second faces are covered in a conductive surface coating.

12. A measuring device according to claim 10, wherein said stack structure comprises first and second electrical connection means for respectively connecting said first and second faces of the sensitive plate to the generator, the first connection means comprising a conductive plate covering the second face of said sensitive plate.

13. A measuring device according to claim 10, wherein said stack structure further comprises at least one plate of PTFE, said plate covering the first face of the sensitive plate.

14. Measuring apparatus comprising: a measuring device according to claim 1; means for measuring the propagation speed of a wave train passing through the substance flowing in said empty space or in a pipe portion situated upstream or downstream from said space; and a calculation unit for determining the density of said substance from the measured propagation speed and impedance.

15. Measuring apparatus according to claim 14, wherein said means for measuring propagation speed comprise an ultrasound emitter and receiver disposed facing each other at the periphery of said empty space or of said pipe portion.

16. Measuring apparatus according to claim 14, wherein said means for measuring propagation speed comprise two transducers of the measuring device, said transducers being disposed facing each other.

* * * * *